United States Patent [19]

Wise et al.

[11] 4,218,455
[45] Aug. 19, 1980

[54] 1-(4-FLUOROPHENYL)-4-[1,2,3,6-TETRAHYDRO-4-(PHENYLTHIO)-1-PYRIDINYL]-BUTANONES AND RELATED SULFOXIDES AND SULFONES

[75] Inventors: Lawrence D. Wise, Ann Arbor, Mich.; Patrick F. Flynn, Wilmington, Del.; Glenn C. Morrison, Ann Arbor, Mich.

[73] Assignee: Warner-Lambert Company, Morris Plains, N.J.

[21] Appl. No.: 922,511

[22] Filed: Jul. 10, 1978

[51] Int. Cl.$^2$ .................. A61K 31/44; C07D 213/04
[52] U.S. Cl. ............................ 424/263; 546/294; 546/301
[58] Field of Search ................ 546/301, 294; 424/263

[56] References Cited
U.S. PATENT DOCUMENTS

| | | | |
|---|---|---|---|
| 4,128,552 | 12/1978 | Wise et al. | 546/294 |
| 4,134,982 | 1/1979 | Wise et al. | 424/263 |

*Primary Examiner*—Alan L. Rotman
*Attorney, Agent, or Firm*—Albert H. Graddis; George M. Kaplan

[57] ABSTRACT

Tetrahydropyridylbutyrophenones of the following formula IX:

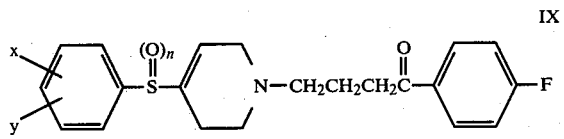

wherein x is hydrogen, halogen such as fluorine, chlorine, bromine or iodine, trifluoromethyl, alkoxy, nitro, cyano, amino, lower alkyl of 1 to 6 carbons, aryl or substituted aryl; y is hydrogen or halogen; and n is 0, 1 or 2; and the non-toxic, pharmaceutically acceptable acid addition salts thereof. Tetrahydropyridylbutanols having the formula X:

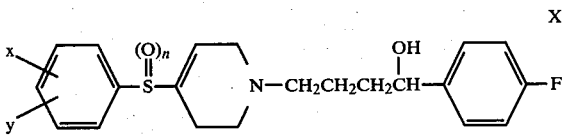

wherein x and y are as defined above, as well as their non-toxic, pharmaceutically acceptable acid addition salts, are also disclosed. The compounds of the invention having the formulas IX and X are useful as antipsychotics.

13 Claims, No Drawings

1-(4-FLUOROPHENYL)-4-[1,2,3,6-TETRAHYDRO-4-(PHENYLTHIO)-1-PYRIDINYL]-BUTANONES AND RELATED SULFOXIDES AND SULFONES

This invention relates to tetrahydropyridylbutyrophenones of the following formula IX:

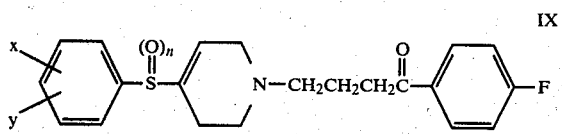

wherein X is hydrogen, halogen such as fluorine, chlorine, bromine or iodine, trifluoromethyl, alkoxy, nitro, cyano, amino, lower alkyl of 1 to 6 carbons, aryl or substituted aryl; y is hydrogen or halogen and n is 0, 1 or 2.

Also embraced within the scope of this invention are the non-toxic, pharmaceutically acceptable acid addition salts of the aforementioned bases of the formula IX.

The compounds of the invention having the formula IX are prepared starting with an appropriate 4-phenylthiopyridine of formula I:

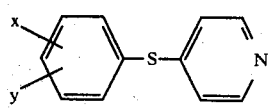

which is reduced to its corresponding 1,2,3,6-tetrahydropyridine (formula II below) with aluminum hydride in an appropriate solvent such as ether or tetrahydrofuran:

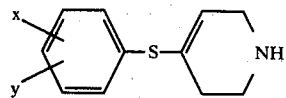

Alkylation of the 1,2,3,6-tetrahydropyridine II with 4-halo-p-fluorobutyrophenone, typically with 4-chloro-p-fluorobutyrophenone provides a tetrahydropyridylbutyrophenone having formula III below:

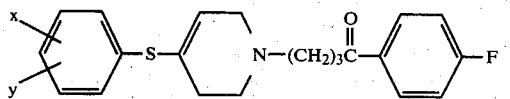

The tetrahydropyridylbutyrophenone III is then treated with one equivalent of an oxidizing agent such as hydrogen peroxide in acetic acid to obtain a sulfoxide having the formula IV:

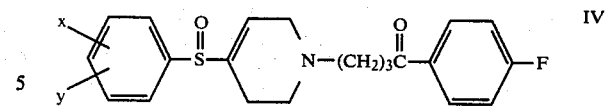

By treating the tetrahydropyridylbutyrophenone III with an excess of aforementioned oxidizing agent, a corresponding sulfone having the formula V is obtained:

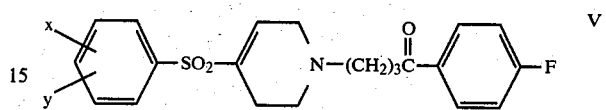

In the above formulas I, II, III, IV and V, x and y are as defined above in formula IX.

Compounds of the invention having the formula X:

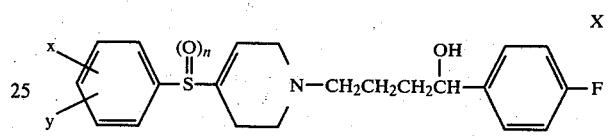

wherein x is hydrogen, halogen, such as fluorine, chlorine, bromine, or iodine, trifluoromethyl, alkoxy, nitro, cyano, amino, lower alkyl of 1 to 6 carbons, aryl or substituted aryl; y is hydrogen or halogen; and n is 0, 1 or 2; and the non-toxic, pharmaceutically acceptable acid addition salts thereof, are prepared by subjecting the tetrahydropyridylbutyrophenone III to sodium borohydride reduction to obtain a butanol derivative having formula VI below:

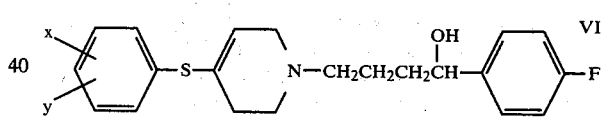

By treating the butanol derivative VI with one equivalent of an oxidizing agent such as hydrogen peroxide—acetic acid, one obtains a sulfoxide having the formula VII:

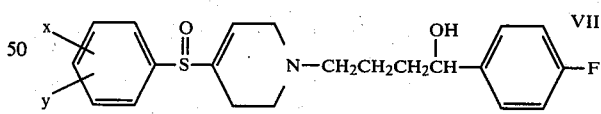

If the butanol derivative VI is treated with an excess of aforementioned oxidizing agent, a corresponding sulfone of formula VIII is obtained:

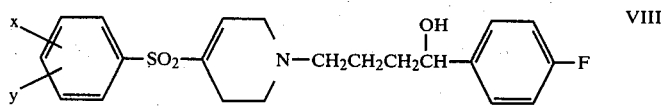

In the above formulas VI, VII and VIII, x and y have the same meaning as defined above for formula X.

The starting compound I above, in which x and y are hydrogen, is described in the Journal of American Chemical Society, Volume 59, Page 2697 (1937)

whereas where x is chloro and y is hydrogen, such a compound is described in Belgian Pat. No. 618,679 (1962). The disclosures in these references are incorporated herein. Other analogs of I are prepared in the same manner as described in these references, or by obvious chemical variations thereof, typically by reacting an appropriately substituted thiophenol with 4-chloropyridine.

Acid addition salts of the compounds of the subject invention having the formulas IX and X are prepared by treating these compounds with an acid such as hydrochloric, hydrogen iodide, nitric, sulfuric, oxalic, tartaric and the like in stoichiometric amounts. These salts are recovered from reaction mixtures of methods known in the art. Of the above mentioned salts, the hydrochloride, oxalate and tartrate salts are preferred.

In the above definition for x and y, halogen is meant to include all four members, i.e., fluorine, chlorine, bromine and iodine. Lower alkyl and the lower alkyl portion of lower alkoxy has 1 to 6 carbon atoms as exemplified by methyl, ethyl, propyl, isopropyl and so on. Aryl is preferably an aromatic hydrocarbon of 6 to 10 carbon atoms such as phenyl or naphthyl. The aryl may be optionally substituted by groups such as the aforesaid halogen, nitro, amino, lower alkyl or lower alkoxy.

The compounds of the present invention having formulas IX and X, exhibit a pharmaceutical profile resembling known antipsychotics such as, for example, haloperidol or pimozide.

For example, in a test conducted in accordance with the procedure known as the Sidman Avoidance Screen, M. Sidman, Science, 118, 157 (1953), the compound of the present invention having the formula IX, in which y is para-fluoro and n is 1 (Example 9), is active in rats at a dose of about 1 mg/kg, intraperitoneally. The compounds of this invention are further distinguished over other known antipsychotics in that they exhibit a low incidence of extrapyramidal side effects, which are undesirable side effects associated with known antipsychotics, e.g., haloperidol or pimozide.

The compounds of the invention are indicated in the management of psychotic disorders such as schizophrenia in mammals. Generally, a dose of 1–50 mg. orally or by injection, one to three times daily is suggested. This dosage regimen may be varied depending upon the severity of the condition and according to individual needs.

The compounds of this invention are formulated into dosage forms suitable for oral administration, such as tablets and syrup, by methods well-known to the pharmacist's art. They can also be administered in the form of suppositories, which are also formulated by methods well-known in the pharmacist's art. For parenteral administration, the salts of the above compounds are preferable. They are formulated by dissolving the salt in water, sterilizing and packaging into individual ampules.

To further illustrate the practice of this invention, the following Examples are included:

EXAMPLE 1

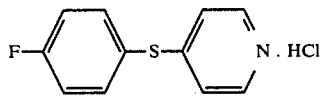

4-[(4-Fluorophenyl)thio]pyridine hydrochloride.

To 50.0 g of 4-fluorobenzenethiol cooled in an ice bath at 0° was slowly added 44.3 g of 4-chloropyridine. After several minutes, a vigorous reaction ensued with the formation of a white solid. The product was washed with ether and dried to yield 87.2 g (92.8%) of white powder, m.p. 217°–220°. Recrystallization from isopropanol gave white needles, m.p. 224°–226°.

Anal. Calcd. for $C_{11}H_8FNS.HCl$: C, 54.66; H, 3.75; Cl, 14.67; F, 7.86; N, 5.80; S, 13.27. Found: C, 54.58; H, 3.77; Cl, 14.84; F, 7.75; N, 5.77; S, 13.36.

Employing the procedure described in the above example, the following compounds were also prepared:

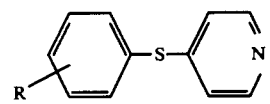

| R | Formula | Anal. | m.p. |
|---|---|---|---|
| p-F | $C_{11}H_8FNS . HCl$ | CHClFNS | 224°–226° |
| p-Br | $C_{11}H_8BrNS . HCl$ | CHBrClNS | 233°–235° |
| p-NO$_2$ | $C_{11}H_8N_2O_2S . HCl$ | CHClNS | 256°–258° |
| p-OCH$_3$ | $C_{12}H_{11}NOS$ | CHNS | 95°–97° |
| p-CH$_3$ | $C_{12}H_{11}NS . HCl$ | CHClNS | 238°–240° |
| m-CF$_3$ | $C_{12}H_8F_3NS . HCl$ | CHClFNS | 190°–192° |
| o,o-diCl | $C_{11}H_7Cl_2NS . HCl$ | CHClNS | 220°–222° |
| o-Cl | $C_{11}H_8ClNS . HCl$ | CHClNS | 227°–229° |
| m-Cl | $C_{11}H_8ClNS . HCl$ | CHClNS | 82°–84° |

EXAMPLE 2

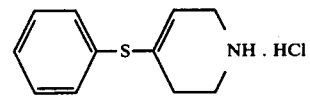

4-(Phenylthio)-1,2,3,6-tetrahydropyridine Hydrochloride

To a suspension of 7.00 g of lithium aluminum hydride in 200 ml of ether is added a solution of 7.75 g of aluminum chloride in 150 ml of ether. After the mixture is stirred for 30 minutes, a solution of 20.0 g of 4-(phenylthio)-pyridine in 100 ml of ether is slowly added, and the reaction mixture is refluxed for 4 hours. The excess aluminum hydride is destroyed by careful addition of water. The mixture is filtered, and the filtrate is evaporated. Distillation of the residue yields 16.5 g (80.9%) of yellow oil, b.p. 112°–114° C. (0.25 mm). The hydrochloride is formed in ether, m.p. 161°–164° C. Recrystallization from isopropanol affords white crystals, m.p. 161°–163° C.

Anal. Calcd. for $C_{11}H_{13}NS.HCl$: C, 58.01; H, 6.20; Cl, 15.57; N, 6.15; S, 14.08. Found: C, 58.20; H, 6.30; Cl, 15.66; N, 5.95; S, 14.29.

EXAMPLE 3

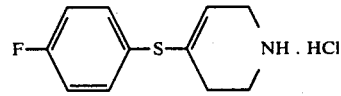

4-[(4-Fluorophenyl)thio]-1,2,3,6-tetrahydropyridine Hydrochloride

According to the procedure for synthesis of 4-(phenylthio)-1,2,3,6-tetrahydropyridine, 58.5 g of 4-[(4-fluorophenyl)thio]pyridine is reduced with aluminum hydride. The crude oil is treated with ethereal hydrogen chloride to give 58.2 g (83.1%) of white powder, m.p. 136°-142° C. Recrystallization from acetonitrile gives white crystals, m.p. 158°-159° C.

Anal. Calcd. for $C_{11}H_{12}FNS \cdot HCl$: C, 53.76; H, 5.33; Cl, 14.43; F, 7.73; N, 5.70; S, 13.05. Found: C, 53.75; H, 5.37; Cl, 14.38; F, 7.53; N, 5.73; S, 13.17.

EXAMPLE 4

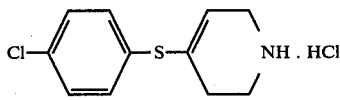

4-[(4-Chlorophenyl)thio]-1,2,3,6-tetrahydropyridine Hydrochloride.

The product is prepared according to the procedure for the synthesis of 4-[(4-fluorophenyl)thio]-1,2,3,6-tetrahydropyridine hydrochloride by reducing 26.3 g of 4-[(4-chlorophenyl)thio]pyridine with aluminum hydride. The hydrochloride salt is generated in ether from the crude oil to afford a light tan powder, m.p. 174°-175° C.

Anal. Calcd. for $C_{11}H_{12}ClNS \cdot HCl$: C, 50.39; H, 5.00; Cl, 27.04; N, 5.34; S, 12.23. Found: C, 50.61; H, 5.04; Cl, 27.22; N, 5.30; S, 12.21.

EXAMPLE 5

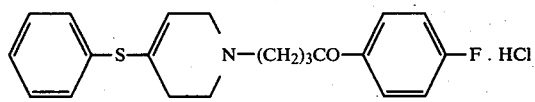

1-(4-Fluorophenyl)-4-[1,2,3,6-tetrahydro-4-(phenylthio)-1-pyridinyl]-butanone Hydrochloride.

A mixture of 16.7 g of 4-(phenylthio)-1,2,3,6-tetrahydropyridine, 17.6 g of 4-chloro-p-fluorobutyrophenone and 20 g of potassium carbonate in 200 ml of toluene is refluxed for 48 hours. The inorganic salts are separated by filtration. The filtrate is evaporated, and the residue is treated with dilute hydrochloric acid. The resulting precipitate is collected to afford 12.5 g (36.4%) of tan powder, m.p. 165°-170° C. dec. Three recrystallizations from acetonitrile gives tan plates, m.p. 172°-174° C. dec.

Anal. Calcd. for $C_{21}H_{22}FNOS \cdot HCl$: C, 64.19; H, 6.16; Cl, 9.02; F, 4.84; N, 3.57; S, 8.16. Found: C, 64.46; H, 6.01; Cl, 9.04; F, 4.70; N, 3.63; S, 8.26.

EXAMPLE 6

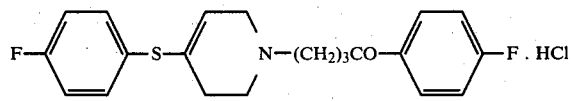

1-(4-Fluorophenyl)-4-{4-[(4-Fluorophenyl)thio]-1,2,3,6-tetrahydro-1-pyridinyl}butanone Hydrochloride.

A solution of 10.4 g of 4-[(4-fluorophenyl)thio]-1,2,3,6-tetrahydropyridine and 12.0 g of 4-chloro-p-fluorobutyrophenone in 100 ml of triethylamine is refluxed for 24 hours. The reaction solution is poured into water and extracted with methylene chloride. The organic extracts are dried over anhydrous sodium sulfate and evaporated. Treatment of residue with excess 1 N hydrochloric acid affords a crude solid. The product is collected, washed well with ether and dried to give 14.1 g (68.8%) of tan powder, m.p. 197°-201° C. Recrystallization from ethanol gives white crystals, m.p. 206°-208° C.

Anal. Calcd. for $C_{21}H_{21}F_2NOS \cdot HCl$: C, 61.53; H, 5.41; Cl, 8.65; F, 9.27; N, 3.42; S, 7.82. Found: C, 61.47; H, 5.42; Cl, 8.81; F, 9.20; N, 3.32; S, 7.87.

EXAMPLE 7

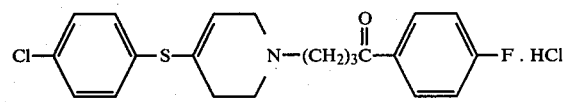

4-{4-[(4-Chlorophenyl)thio]-1,2,3,6-tetrahydro-1-pyridinyl}-1-(4-fluorophenyl)-1-butanone Hydrochloride.

A mixture of 11.2 g of 4-[(4-chlorophenyl)thio]-1,2,3,6-tetrahydropyridine, 10.0 g of 4-chloro-p-fluorobutyrophenone and 6.9 g of potassium carbonate is heated at 98° C. for 1 hour. The mixture is taken up in benzene and filtered. Evaporation of the filtrate gives a brown oil which is treated with a large excess of 1 N hydrochloric acid. The resulting precipitate is collected to afford 8.9 g (46%) of tan powder, m.p. 208°-210° C. Recrystallization from acetonitrile yields off-white crystals, m.p. 220°-222° C.

Anal. Calcd. for $C_{21}H_{21}ClFNOS \cdot HCl$: C, 59.16; H, 5.20; Cl, 16.63; F, 4.46; N, 3.29; S, 7.52. Found: C, 58.93; H, 5.24; Cl, 16.75; F, 4.33; N, 3.22; S, 7.81.

EXAMPLE 8

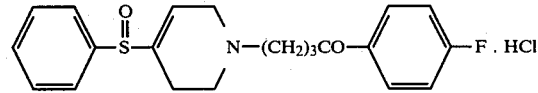

1-(4-Fluorophenyl)-4-[1,2,3,6-tetrahydro-4-(phenylsulfinyl)-1-pyridinyl]-1-butanone Hydrochloride.

To a solution of 7.00 g of 1-(4-fluorophenyl)-4-[1,2,3,6-tetrahydro-4-(phenylthio)-1-pyridinyl]-1-butane hydrochloride in 50 ml of glacial acectic acid is added 1.96 g of 30% aqueous hydrogen peroxide. The solution is allowed to stand at room temperature for 48 hours. Evaporation of the solvent in vacuo gives an oil which is triturated with methanol-ether (1:1). The resulting solid is collected to yield 7.10 g (97.5%) of tan powder, m.p. 187°-189° C. Two recrystallizations from acetonitrile followed by one from isopropanol gives tan powder, m.p. 189°-191° C.

Anal. Calcd. for $C_{21}H_{22}FNO_2S \cdot HCl$: C, 61.68; H, 5.92; Cl, 8.67; F, 4.65; N, 3.43; S, 7.84. Found: C, 61.80; H, 5.81; Cl, 8.89; F, 4.62; N, 3.61; S, 7.84.

EXAMPLE 9

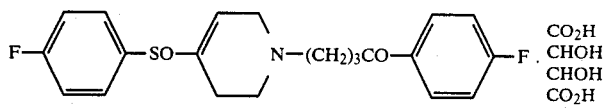

1-(4-Fluorophenyl)-4-{4-[(4-fluorophenyl)sulfinyl]-1,2,3,6-tetrahydro-1-pyridinyl}butanone 2,3-Dihydroxybutanedioate To a solution of 10.0 g of 1-(4-fluorophenyl)-4-{4-[(4-fluorophenyl)thio]-1,2,3,6-tetrahydro-1-pyridinyl}butanone hydrochloride in 75 ml of glacial acetic acid at room temperature is added dropwise a solution of 2.77 g of 30% hydrogen peroxide in 25 ml of acetic acid over 20 minutes. The solution is allowed to stand at room temperature for 48 hours after which the solvent is removed in vacuo. The residue is neutralized with aqueous sodium bicarbonate, and the product is extracted into methylene chloride. The organic extracts is dried over anhydrous sodium sulfate and evaporated to give an orange oil. The oil is treated with methanolic tartaric acid. Crystallization is induced, and the product is collected to yield 9.00 g (66.2%) of white powder, m.p. 151°–154° C. Recrystallization from methanol gives white crystals, m.p. 154°–155° C.

Anal. Calcd. for $C_{21}H_{21}F_2NO_2S.C_4H_6O_6$: C, 55.65; H, 5.04; F, 7.04; N, 2.59; S, 5.94. Found: C, 55.51; H, 5.09; F, 7.04; N, 2.49; S, 6.01.

EXAMPLE 10

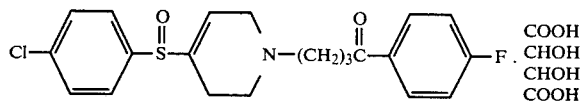

4-{4-[(4-Chlorophenyl)sulfinyl]-1,2,3,6-tetrahydro-1-pyridinyl}-1-(4-fluorophenyl)-1-butanone 2,3-dihydroxybutanedioate A solution of 7.5 g of 4-{4-[(4-chlorophenyl)thio]-1,2,3,6-tetrahydro-1-pyridinyl}-1-(4-fluorophenyl)-1-butanone hydrochloride, 1.8 g of 30% hydrogen peroxide in 100 ml of acetic acid is allowed to stand at room temperature for 6 days. A small quantity of sodium bisulfite is added after which the acetic acid is removed in vacuo. The residue is neutralized with dilute sodium carbonate solution, and the product extracted into chloroform. The solvent is evaporated to give an oil. The tartrate salt is generated in ether and triturated with boiling ethyl acetate to yield a white powder, m.p. 159°–160° C.

Anal. Calcd. for $C_{21}H_{21}ClFNO_2S.C_4H_6O_6$: C, 54.01; H, 4.90; Cl, 6.38; F, 3.42; N, 2.52; S, 5.77. Found: C, 53.96; H, 4.87; Cl, 6.56; F, 3.29; N, 2.40; S, 5.96.

EXAMPLE 11

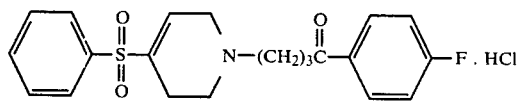

1-(4-Fluorophenyl)-4-[1,2,3,6-tetrahydro-4-(phenylsulfonyl)-1-pyridinyl[-1-butanone Hydrochloride A solution of 10.0 g of 1-(4-fluorophenyl)-4-[1,2,3,6-tetrahydro-4-(phenylthio)-1-pyridinyl]-1-butanone hydrochloride and 28.0 g of 30% hydrogen peroxide in 100 ml of acetic acid is allowed to stand at room temperature. After five days, the excess hydrogen peroxide is reduced by portionwise addition of sodium bisulfite at 0° C., and the acetic acid is distilled in vacuo. The residue is neutralized with 2 N sodium hydroxide, and the product extracted into chloroform. The combined organic extracts are dried over anhydrous sodium sulfate and evaporated to give a light brown oil. Treatment of the oil with ethereal hydrogen chloride affords 6.10 g (61%) of white powder, m.p. 170°–172° C. Recrystallization from isopropanol yields an analytical sample, m.p. 185°–186° C.

Anal. Calcd. for $C_{21}H_{22}FNO_3S.HCl$: C, 59.50; H, 5.47; Cl, 8.36; F, 4.48; N, 3.30; S, 7.56. Found: C, 59.42; H, 5.47; Cl, 8.45; F, 4.26; N, 3.24; S, 7.85.

EXAMPLE 12

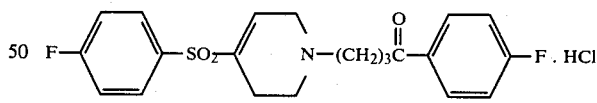

1-(4-Fluorophenyl)-4-{4-[(4-fluorophenyl)sulfonyl]-1,2,3,6-tetrahydro-1-pyridinyl}-1-butanone Hydrochloride Following the procedures of Example 10, 8.0 g of 1-(4-fluorophenyl)-4-{4-[4-fluorophenyl)thio]-1,2,3,6-tetrahydro-1-pyridinyl}-butanone hydrochloride is oxidized with hydrogen peroxide - acetic acid to give 6.70 g (77.9%) of white powder, m.p. 180°–186° C. Recrystallization of the product from ethanol yields white crystals, m.p. 187°–188° C.

Anal. Calcd. for $C_{21}H_{21}F_2NO_3S.HCl$: C, 57.08; H, 5.02; Cl, 8.02; F, 8.60; N, 3.17; S, 7.26. Found: C, 56.93; H, 5.11; Cl, 8.17; F, 8.46; N, 3.20; S, 7.35.

EXAMPLE 13

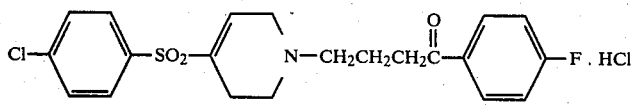

1-(4-Fluorophenyl)-4-{4-[(4-chlorophenyl)sulfonyl]-1,2,3,6-tetrahydro-1-pyridinyl}-1-butanone Hydrochloride Following the procedure of Example 10, 12.3 g of 1-(4-fluorophenyl)-4-{4-[(4-chlorophenyl)thio]-1,2,3,6-tetrahydro-1-pyridinyl}-1-butanone hydrochloride is oxidized with hydrogen peroxide - acetic acid to give 9.10 g (69%) of off-white powder, m.p. 191°–192° C. dec.

Anal. Calcd. for $C_{21}H_{21}ClFNO_3S \cdot HCl$: C, 55.03; H, 4.84; Cl, 15.47; F, 4.15; N, 3.06; S, 7.00. Found: C, 54.86; H, 4.77; Cl, 15.24; F, 3.92; N, 2.98; S, 7.20.

EXAMPLE 14

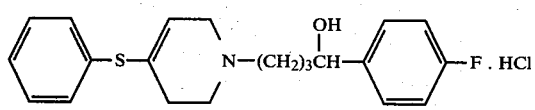

δ-(4-Fluorophenyl)-1,2,3,6-tetrahydro-4-(phenylthio)-1-pyridinebutanol Hydrochloride To 22.7 g of 1-(4-fluorophenyl)-4-[1,2,3,6-tetrahydro-4-(phenylthio)-1-pyridyl]-1-butanone in 150 ml of ethanol is added portionwise with stirring 1.34 g of sodium borohydride over 5 minutes. The solution is stirred for an additional hour after which the solvent is evaporated in vacuo. Water is added to the residue, and the product is extracted into chloroform. The combined organic extracts are dried over anhydrous sodium sulfate. Evaporation of the solution yields a light brown oil which is converted to the hydrochloride salt in ether to give a white powder, m.p. 125°–126° C.

Anal. Calcd. for $C_{21}H_{24}FNOS \cdot HCl$: C, 64.03; H, 6.40; Cl, 9.00; F, 4.82; N, 3.56; S, 8.14. Found: C, 64.03; H, 6.47; Cl, 9.10; F, 5.06; N, 3.33; S, 8.31.

EXAMPLE 15

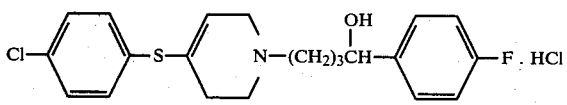

4-[(4-Chlorophenyl)thio]-δ-(4-fluorophenyl)-1,2,3,6-tetrahydro-2-pyridinebutanol Hydrochloride According to the procedure of Example 13, 61.4 g of 4-{4-[(4-chlorophenyl)thio]-1,2,3,6-tetrahydro-1-pyridinyl}-1-(4-fluorophenyl)-1-butanone is reduced with sodium borohydride to yield an orange oil. The hydrochloride salt of the product separated in ether to yield 40.0 g (64%) of white powder, m.p. 40° C. Recrystallization from acetonitrile gives an off-white powder, m.p. 134°–135° C.

Anal. Calcd. for $C_{21}H_{23}ClFNOS \cdot HCl$: C, 58.80; H, 5.64; Cl, 16.53; F, 4.43; N, 3.27; S, 7.48. Found: C, 58.64; H, 5.69; Cl, 16.57; F, 4.23; N, 3.17; S, 7.56.

EXAMPLE 16

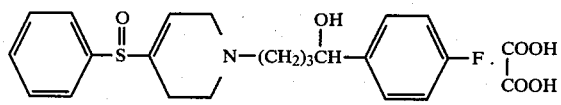

δ-(p-Fluorophenyl)-1,2,3,6-tetrahydro-4-(phenylsulfinyl)-1-pyridinebutanol ethanedioate To a solution of 2.84 g of δ-(4-fluorophenyl)-1,2,3,6-tetrahydro-4-(phenylthio)-1-pyridinebutanol hydrochloride in 125 ml of acetic acid is added 0.82 g of 30% hydrogen peroxide solution. The resultant solution is allowed to stand at room temperature for 3 days after which the acetic acid is distilled in vacuo. The residue is neutralized with aqueous sodium carbonate, and the product is extracted into chloroform. The combined organic extracts are dried over anhydrous sodium sulfate and evaporated to yield 3.00 g of brown oil. The oxalate salt is formed in ether. The product is triturated in ethyl acetate to give 1.0 g (30%) of white powder, m.p. 131°–133° C.

Anal. Calcd. for $C_{21}H_{24}FNO_2S \cdot C_2H_2O_4$: C, 59.60; H, 5.65; F, 4.10; N, 3.02; S, 6.92. Found: C, 59.45; H, 5.77; F, 3.92; N, 2.81; S, 7.20.

EXAMPLE 17

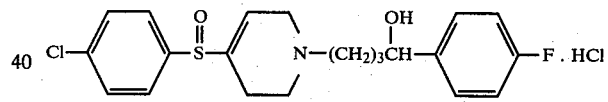

δ-(3-{4-[(4-Chlorophenyl)sulfinyl]-1,2,3,6-tetrahydro-1-pyridinyl}propyl)-4-fluorobenzenemethanol hydrochloride According to the procedure of Example 15, 8.0 g of 4-[(4-chlorophenyl)thio]-δ-(4-fluorophenyl)-1,2,3,6-tetrahydro-1-pyridinebutanol hydrochloride is oxidized with 2.12 g of 30% hydrogen peroxide to yield 7.10 g of light green oil. The hydrochloride salt is generated in ether to afford a white powder, m.p. 146°–148° C.

Anal. Calcd. for $C_{21}H_{23}ClFNO_2S \cdot HCl$: C, 56.76; H, 5.44; Cl, 15.96; F, 4.28; N, 3.15; S, 7.22. Found: C, 56.90; H, 5.63; Cl, 15.97; F, 4.07; N, 3.06; S, 7.47.

EXAMPLE 18

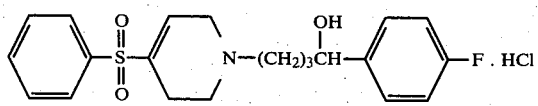

δ-(4-Fluorophenyl)-1,2,3,6-tetrahydro-4-(phenylsulfonyl)-1-pyridinebutanol Hydrochloride To a solution of 7.0 g of δ-(4-fluorophenyl)-1,2,3,6-tetrahydro-4-(phenylthio)-1-pyridinebutanol hydrochloride in 70 ml of acetic acid is added 20.2 g of 30% hydrogen peroxide. After the reaction solution has stood at room temperature for 3 days, the excess oxidant is reduced by portionwise addition of sodium bisulfite at 0° C. The acetic acid is distilled in vacuo. The residue is neutralized with aqueous sodium carbonate, and the product extracted into chloroform. The organic extracts are dried over anhydrous sodium sulfate and evaporated to give an oil. Treatment of the oil with ethereal hydrogen chloride gives a quantitative yield of white powder, m.p. 145°–147° C.

Anal. Calcd. for $C_{21}H_{24}FNO_3S \cdot HCl$: C, 59.22; H, 5.92; Cl, 8.32; F, 4.46; N, 3.29; S, 7.53. Found: C, 59.04; H, 5.92; Cl, 8.38; F, 4.31; N, 3.28; S, 7.52.

EXAMPLE 19

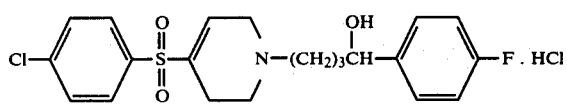

δ-(3-{4-[(4-Chlorophenyl)sulfonyl]-1,2,3,6-tetrahydro-1-pyridinyl}propyl)-4-fluorobenzenemethanol Hydrochloride Following the procedure of Example 17, 4.10 g of 4-[(4-chlorophenyl)thio]-δ-(4-fluorophenyl)-1,2,3,6-tetrahydro-1-pyridinebutanol hydrochloride is oxidized with 10.8 g of 30% hydrogen peroxide. After 5 days at room temperature, the product is isolated as the hydrochloride salt. Recrystallization from acetonitrile-ether affords an off-white powder, m.p. 185°–186° C.

Anal. Calcd. for $C_{21}H_{23}ClFNO_3S \cdot HCl$: C, 54.79; H, 5.25; Cl, 15.40; F, 4.13; N, 3.04; S, 6.69. Found: C, 54.65; H, 5.24; Cl, 15.49; F, 3.92; N, 2.90; S, 7.06.

We claim:

1. A compound having the formula IX:

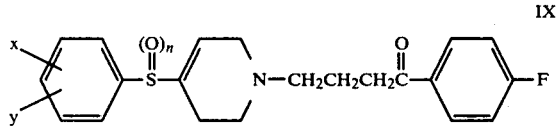

wherein x is hydrogen, halogen, trifluoromethyl, lower alkoxy, nitro, amino, lower alkyl of 1–6 carbons, phenyl, phenyl substituted with halogen, nitro, amino, lower alkyl or lower alkoxy; naphthyl or naphthyl substituted with halogen, nitro, amino lower alkyl or lower alkoxy; y is hydrogen or halogen; and n is 0, 1 or 2; and the non-toxic, pharmaceutically acceptable acid addition salts thereof.

2. The compound according to claim 1 wherein x is hydrogen or halogen and y is hydrogen.

3. The compound according to claim 1 which is 1-(4-fluorophenyl)-4-[1,2,3,6-tetrahydro-4-(phenylthio)-1-pyridinyl]-butanone hydrochloride.

4. The compound according to claim 1 which is 1-(4-fluorophenyl)-4-{4-[(4-fluorophenyl)thio]-1,2,3,6-tetrahydro-1-pyridinyl}butanone hydrochloride.

5. The compound according to claim 1 which is 4-{4-[(4-Chlorophenyl)thio]-1,2,3,6-tetrahydro-1-pyridinyl}-1-(4-fluorophenyl)-1-butanone Hydrochloride.

6. The compound according to claim 1 which is 1-(4-Fluorophenyl)-4-[1,2,3,6-tetrahydro-4-(phenylsulfinyl)-1-pyridinyl]-1-butanone Hydrochloride.

7. The compound according to claim 1 which is 1-(4-Fluorophenyl)-4-{4-[(4-fluorophenyl)sulfinyl]-1,2,3,6-tetrahydro-1-pyridinyl}butanone 2,3-Dihydroxybutanedioate.

8. The compound according to claim 1 which is 4-{4-[4-Chlorophenyl)sulfinyl]-1,2,3,6-tetrahydro-1-pyridinyl}-1-(4-fluorophenyl)-1-butanone 2,3-Dihydroxybutanedioate.

9. The compound according to claim 1 which is 1-(4-Fluorophenyl)-4-[1,2,3,6-tetrahydro-4-(phenylsulfonyl)-1-pyridinyl]-1-butanone hydrochloride.

10. The compound according to claim 1 which is 1-(4-Fluorophenyl)-4-{4-[(4-fluorophenyl)sulfonyl]-1,2,3,6-tetrahydro-1-pyridinyl}-1-butanone Hydrochloride.

11. The compound according to claim 1 which is 1-(4-fluorophenyl)-4-{4-[(4-chlorophenyl)sulfonyl]-1,2,3,6-tetrahydro-1-pyridinyl}-1-butantone hydrochloride.

12. A pharmaceutical composition for treating psychotic conditions which comprises an effective amount of a compound having the formula IX:

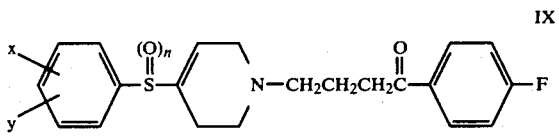

wherein x is hydrogen, halogen, trifluoromethyl, lower alkoxy, nitro, amino, lower alkyl of 1–6 carbons, phenyl, phenyl substituted with halogen, nitro, amino, lower alkyl or lower alkoxy; naphthyl or naphthyl substituted with halogen, nitro, amino, lower alkyl or lower alkoxy; y is hydrogen or halogen; and n is 0, 1 or 2; and the non-toxic, pharmaceutically acceptable acid addition salts thereof together with an inert pharmaceutical carrier therefor.

13. A method for treating psychotic conditions in mammals which comprises the administration of a sufficient amount of a compound having the formula IX:

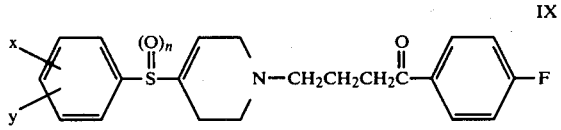

wherein x is hydrogen, halogen, trifluoromethyl, lower alkoxy, nitro, amino, lower alkyl of 1–6 carbons, phenyl, phenyl substituted with halogen, nitro, amino, lower alkyl or lower alkoxy; naphthyl or naphthyl substituted with halogen, nitro, amino, lower alkyl or lower alkoxy; y is hydrogen or halogen; and n is 0, 1 or 2; and the non-toxic, pharmaceutically acceptable acid addition salts thereof.

* * * * *